United States Patent [19]

Sawyer

[11] Patent Number: 5,098,406
[45] Date of Patent: Mar. 24, 1992

[54] ANTI-REFLUX, LOW FRICTION, SKIRTED HEMOSTASIS VALVE AND INTRODUCER

[75] Inventor: Philip N. Sawyer, Brooklyn, N.Y.

[73] Assignee: Interface Biomedical Laboratories Corp., Brooklyn, N.Y.

[21] Appl. No.: 608,081

[22] Filed: Nov. 1, 1990

[51] Int. Cl.⁵ .......................................... A61M 5/315
[52] U.S. Cl. ................................... 604/247; 137/843
[58] Field of Search .............. 604/247, 248, 249, 122, 604/27, 43; 137/493, 843, 846

[56] References Cited

U.S. PATENT DOCUMENTS

| | | | |
|---|---|---|---|
| 4,684,364 | 8/1987 | Sawyer et al. | 604/123 |
| 4,705,501 | 10/1987 | Wigness et al. | 604/43 |
| 4,722,725 | 2/1988 | Sawyer et al. | 604/27 |
| 4,784,644 | 11/1988 | Sawyer et al. | 604/122 |
| 4,846,806 | 7/1989 | Wigness et al. | 604/175 |
| 4,883,461 | 11/1989 | Sawyer | 604/27 |
| 4,932,633 | 6/1990 | Johnson et al. | 251/149.1 |

*Primary Examiner*—John D. Yasko
*Attorney, Agent, or Firm*—Pennie & Edmonds

[57] ABSTRACT

A fluid flow control device of tubular means having fluid input means and fluid output means connected by a bore constituting a flow channel, means for maintaining the bore in a normally closed position, the bore being forcible to an open position in response to insertion of a medical device into the fluid input means and past the maintaining means, the maintaining means being constructed and arranged to return the bore to the closed position when the medical device is removed therefrom; and means for prevention of fluid reflux or blood from the fluid output means toward the fluid input means when the bore is in the open position.

18 Claims, 2 Drawing Sheets

ANTI-REFLUX, LOW FRICTION, SKIRTED HEMOSTASIS VALVE AND INTRODUCER

FIELD OF THE INVENTION

This invention relates to a method and means for preventing the reflux of fluid including blood through fluid flow control means in a transcutaneous introducer catheter. Also, the invention relates to a method for increasing the tactile sensation and manipulating ability of a medical device which is used in conjunction with the transcutaneous hemostasis valved introducer catheter.

BACKGROUND OF THE INVENTION

The majority of instrumentations of blood vessels are carried out transcutaneously. In most instances, this requires the use of a transcutaneous introducer catheter, hereinafter referred to as the introducer. The introducer remains in the vessel of the patient during the course of the operation to provide the operating physician with means to insert and remove various medical apparatus efficiently. A problem arises in that once the introducer catheter is inserted into the vessel, the blood in the vessel is able to flow freely out of the invaded vessel through the introducer. In the past, in order to prevent the reflux of blood from the introducer, the physician placed his finger over the outlet of the introducer.

In response to the aforementioned problem, several diaphragm valves have been developed to prevent the reflux of fluid from the introducer upon insertion into the vessel. These diaphragm valves operate in conjunction with the introducer. They generally contain a small hole so various medical devices can be introduced by the physician through the introducer and into the vessel. The diaphragm valve surrounds the inserted apparatus for example, a catheter, thereby preventing the reflux of fluid out of the introducer. To prevent blood reflux, it is necessary for the diaphragm valve to fit snugly around the medical apparatus. However, as a result of the high friction level required between the diaphragm valve and the inserted device to prevent the reflux of blood (i.e., controlled bleeding), the tactile sensation and ability to manipulate and maneuver the device by the physician are reduced. While the diaphragm valve reduces the reflux of fluid, the problems associated with the high friction level are undesirable.

A number of patents disclose fluid flow control devices. U.S. Pat. No. 4,705,501 discloses a bidirectional anti-reflux vascular access system for the infusion of liquids into a body or for the aspiration removal of liquid samples from the body. A catheter formed from a pair of concentric inner and outer tubes is used as a fluid control. The inner tube is partially collapsed and closed at its distal end. The outer tube closely engages the inner tube and defines a catheter lumen therewith when the inner tube is collapsed by evacuation. To prevent movement of the tubes relative to each other, the inner and outer tubes are joined longitudinally over a small portion of the circumference of the inner tube. Also, U.S. Pat. No. 4,846,806 discloses an implantable intravascular access system which utilizes the catheter of the '501 patent.

U.S. Pat. No. 4,932,633 suggests a hemostasis valve gasket for use in the introducer. This gasket is formed from a resilient elastomeric material which is designed to close about small objects, such as a guide wire, as well as about larger objects, such a working catheter to prevent air or blood leakage. The gasket includes an angled slit in a central member which is positioned between proximal and distal cylindrical members each having a central bore in alignment with the angled slit. While satisfactory for certain applications, this gasket must be separately manufactured and located within the introducer, which adds cost and complexity to the overall device. Function, moreover, is friction dependent.

In U.S. Pat. No. 4,684,364, there is disclosed a flow control device having a tubular structure with input means and output means each provided with an open bore, channel means connecting the input and output bores and operating between open and closed positions, and clip means for retaining a portion of the channel means in a prestressed condition to obturate the channels means so as to maintain it in a closed position. The channel means is forcible to an open position in response to a positive pressure in either one of the bores to facilitate flow through the channel means from the bore containing the positive pressure to the other bore. Also, the flow control device is capable of passing fluid in either direction depending upon which bore contains the positive pressure, with the clip means returning the channel means to the closed position when the positive fluid pressure is removed.

U.S. Pat. No. 4,722,725 discloses a catheter means comprising an elongated body portion for insertion into a patient, at least one integral hub portion adjacent to the body portion, and at least one fluid flow control means located in either the body or hub portion adjacent to the body portion, and at least one fluid flow control means located in either the body or hub portion or adjacent to the hub portion. The fluid flow control means may be integral with or releasably secured to its respective hub portion. Also, obturating means for rendering incompetent the fluid flow control means can be used.

In U.S. Pat. No. 4,784,644, there is disclosed a novel valve comprising a disc member for use in a fluid flow control means. This fluid flow control means can be incorporated into a catheter and used for delivering or removing fluids to or from a patient.

U.S. Pat. No. 4,883,461 discloses a fluid flow control means incorporated into a catheter, with the control means comprising a disc valve.

The fluid flow control means described in the four preceding patents may not completely prevent the reflux of fluid from a vessel. In the neutral position, the disk valve is competent and no reflux of fluid can occur. However, when the physician inserts a medical apparatus, hereinafter referred to as a device, into an introducer which includes the valve, the valve will become partially incompetent. For example, when the physician inserts a catheter into the introducer, the disk is pushed aside, creating small areas on either side of the catheter which can permit the reflux of fluid.

Accordingly, the present invention is directed to a new and effective method for preventing the reflux of fluids associated with the introduction of a catheter system into the vascular tree, said system comprising a transcutaneous introducer catheter. In addition, the present invention provides means for increasing the tactile sensation and manipulating ability of a device operated in conjunction with a transcutaneous introducer catheter. In order to prevent the reflux of fluid through or around these devices, the present invention incorporates the use of an integral skirt or molded plug which forms around the hemostatic seal around the device when it is inserted in the catheter valve.

SUMMARY OF THE INVENTION

The present invention relates to fluid flow control means for preventing the reflux of fluid from the patient after insertion of a medical device into the patient's vascular system.

Another feature of the present invention relates to a method for reducing the friction level between the fluid reflux prevention means portion of the fluid flow control means and the device which is inserted thereinto, thereby increasing the tactile sensation and manipulating ability of the device.

The fluid reflux prevention means preferably is fluid flow control means comprising a tubular means with fluid input means and fluid output means; valve means located within the tubular means having an open and closed position, the valve remaining competent in response to fluid reflux but is forced to an open position when a device is inserted into the catheter, and skirt means located within the tubular means, wherein said skirt acts to form a hemostatic seal around the inserted device to prevent the reflux of fluid from the introducer when the valve is open. This method further contemplates that the skirt means is competent to fluid reflux when the device is inserted into the introducer.

The methods of the invention advantageously utilize a fluid flow control means comprising a valve means and a skirt means for prevention of fluid reflux from the introducer. The valve means comprises a tube having a flexible plastic disc therein, having an open and closed position. When there is no device inserted into the introducer the valve is competent, thereby preventing the reflux of fluid. Upon insertion of a device into the introducer, the disc is bypassed and opened to allow insertion of the device into the vessel, thereby creating small areas around the device which may permit the reflux of fluid. This possibility of the reflux of fluid is eliminated by the skirt means.

The skirt means which is located between the valve means and the output chamber works in conjunction with the valve means to prevent the reflux of fluid. In particular, when a device is inserted into the introducer, the device may render the valve means incompetent, as described above. In any event, the skirt means collapses around the inserted device forming a hemostatic seal with the device. The hemostatic seal formed by the skirt prevents the fluid in the vessel from contacting the incompetent valve means, thereby preventing the reflux of fluid including blood.

In one embodiment of the invention, the skirt means is comprised of a funnel shaped soft collapsible silicone cone having a small central hole to permit the device which is inserted into the vessel, to pass through the skirt means. The funnel shaped skirt is positioned in the tubular means so that the diameter of the skirt narrows as the distance from the valve means increases. Thus, at the point of the skirt means farthest from the valve means and closest to the vessel, the funnel shaped skirt exhibits its smallest diameter. This is also the location of the small hole of the skirt means.

As a device is inserted into the introducer, the device opens the valve means and proceeds to pass through the skirt means via the hole, in route to the vessel, whereupon the silicone skirt collapses around the device to form the hemostatic seal. The hemostatic seal formed by said skirt and the inserted device prevent fluid from contacting the valve means, thereby preventing any reflux of fluid. In addition, any fluid flowing in the direction from the vessel toward the skirt means, encounters a skirt means of minimal diameter whereby the fluid is directed to the sides of the skirt. Thus, fluid pressure level at the contact point between the device and the skirt is minimized, thereby reducing the possibility of seal failure due to fluid pressure increase.

Also advantageously, the reflux means of the introducer comprising the valve means and the skirt means provides for minimum friction between the reflux means and the inserted device. Due to the described shape and geometry of the skirt means, the reflux of fluid is prevented by redirecting the fluid pressure points between the reflux means and fluid from vessel to points other than the contact point between said skirt means and the inserted device. This redirection of fluid pressure away from said contact point allows the reflux means to be secured to the inserted device with minimal force thereby reducing the friction level between the reflux means and the inserted device. The reduced friction level between the reflux means and the inserted device produces increased tactile sensation and opportunity to manipulate and maneuver the device by the operating physician.

In another embodiment of the invention, the skirt means comprises a diaphanous filamentous tube whereby gravity collapses the said tube around the inserted device. The diaphanous filamentous tube functions in an equivalent manner as the collapsible silicone skirt described above.

DETAILED DESCRIPTION OF THE PREFERRED EMBODIMENTS

To the extent that the disclosure of any of U.S. Pat. Nos. 4,684,364, 4,722,725, 4,784,644 or 4,883,461 is necessary for an understanding of the present invention, the disclosures of these patents are expressly incorporated herein by reference thereto.

Figure 1:
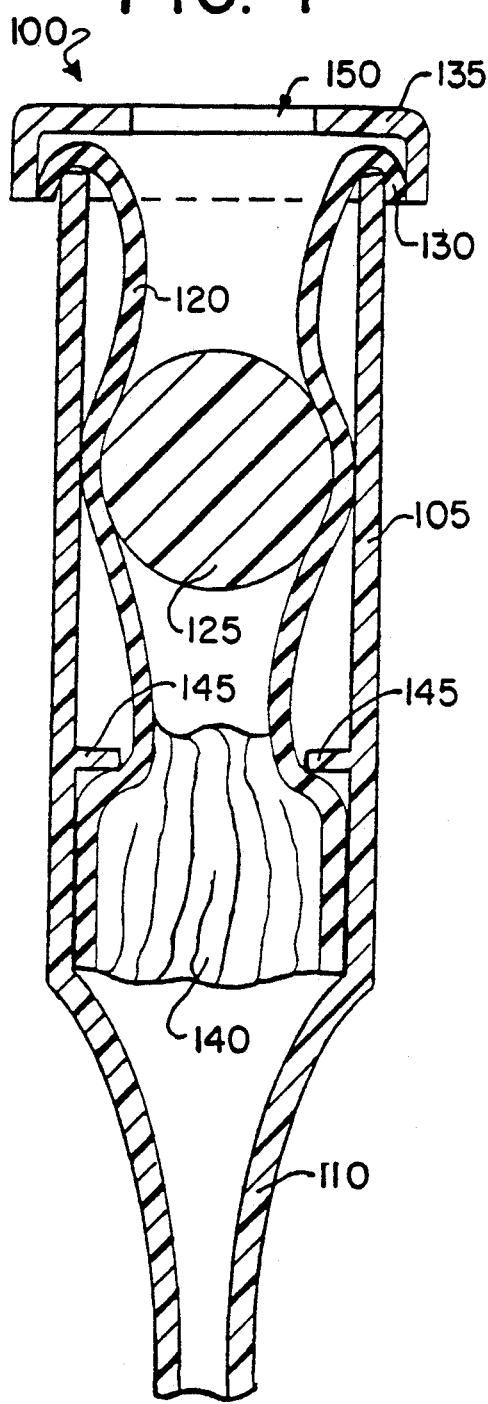
FIG. 1 is a cross-sectional view of a first valve arrangement illustrating a skirt member for preventing fluid reflux.

FIG. 1 is a cross-sectional illustration of a fluid flow control valve 100 in accordance with the present invention. This device includes an outer relatively rigid plastic housing 105 which is cylindrical in form and which terminates in a tapered section 110 for delivery of fluid to a conduit or other transport member for introduction to a patient. Inside of housing 105 is a flexible soft silicone tube 120 within which is disposed a disk member 125 for retaining the tube in a flattened position which is competent to the flow of fluid or reflux of blood therethrough. This disk valve operates in a manner similar to that disclosed in U.S. Pat. No. 4,784,644. A first end of the tube 130 is rolled back over the end of housing 105 and is retained in place by a cap member 135 which is press-fit over the tube end 130 and housing 105 junction. The opposite end of tube 120 includes a diaphanous filamentary structure 140 which is also made of a medical grade of silicone and is wider in diameter, such that the tube folds over itself and forms a collapsible skirt which is integral with the lower end of the flexible tube 120. This skirt 140 is retained in position in housing 105 by the use of a shelf member 145 which extends inwardly around the inner circumference of housing 105 in the area shown in the drawing.

The valve of FIG. 1 is made as follows: two identical housing halves are laid side-by-side on a flat surface or other appropriate support. Next, the skirt portion 140 is formed on the end of a flexible silicone tube or is made separately and is joined to the end of tube 120 by gluing or the like. The tube is then placed in one of the housing halves and the first end 130 is allowed to extend out of the housing half. Skirt portion 140 is placed in position distal of shelf member 145. Disk member 125 can then be introduced into the first end 130 of tube 120 and is placed approximately midway along the length of tube 120. Next, the second housing half is placed over the first housing half and is sonically welded together to form a one-piece housing 105. The first end 130 of tubing 120 is then rolled over the forward end of housing 105 and a cap member 135 is placed thereover to force the tubing 130 against the outside circumference of the forward end of housing 105. The drawing figure clearly shows that disk member 125 is not capable of moving towards the distal end of the valve due to the presence of the shelf member 145, nor can it exit the forward end of the valve due to aperture 150 in end cap 135, both of which provide for an opening having smaller dimensions than that of the disk member 125.

After assembly, disk member 125 retains flexible tube 120 in a flattened position and competent to both the introduction of fluids towards the distal end of the valve as well as to blood reflux from the distal valve towards the forward end of the valve.

Although valve 100 is shown as a separate component with a tapered forward section 110 for direction of fluid to a patient, this valve structure can be made integral or separately attached with a catheter as shown in U.S. Pat. Nos. 4,722,725 and 4,883,461. In addition, the valve could be located at the distal end of the catheter. The valve member 100 generally forms a portion of an introducer catheter, preferably located at the proximal end of such catheter.

To access the vascular system of a patient, a needle at the end of the introducer is used to puncture the skin of the patient and to extend the introducer into the patient's blood vessel. At this point the valve remains competent to blood reflux. Next, a guide wire can be inserted into the flow control means and through the introducer into the patient's blood vessel. Guide wire renders incompetent disk member 125 such that it would be possible for blood reflux to exit the valve and the proximal end of the device. However, skirt member 140 engages a guide wire and prevents blood reflux in the manner described above. Thus, flow control means 100 remains competent to blood reflux.

Next, a dilator which includes a disk to prevent blood reflux is inserted over the guide wire and is properly positioned into the patient's blood vessel. A catheter which also includes a disk valve therein to prevent blood reflux can then be fit over the dilator and positioned in the patient's blood vessel at which point, a source of fluid can be connected to the proximal end of the catheter for introduction of such fluids into the blood vessel of the patient. In addition, a needle or other obturating member can be inserted into the catheter to render incompetent the disk valve therein so as to allow blood to be removed from the blood vessel of the patient.

Figure 2:
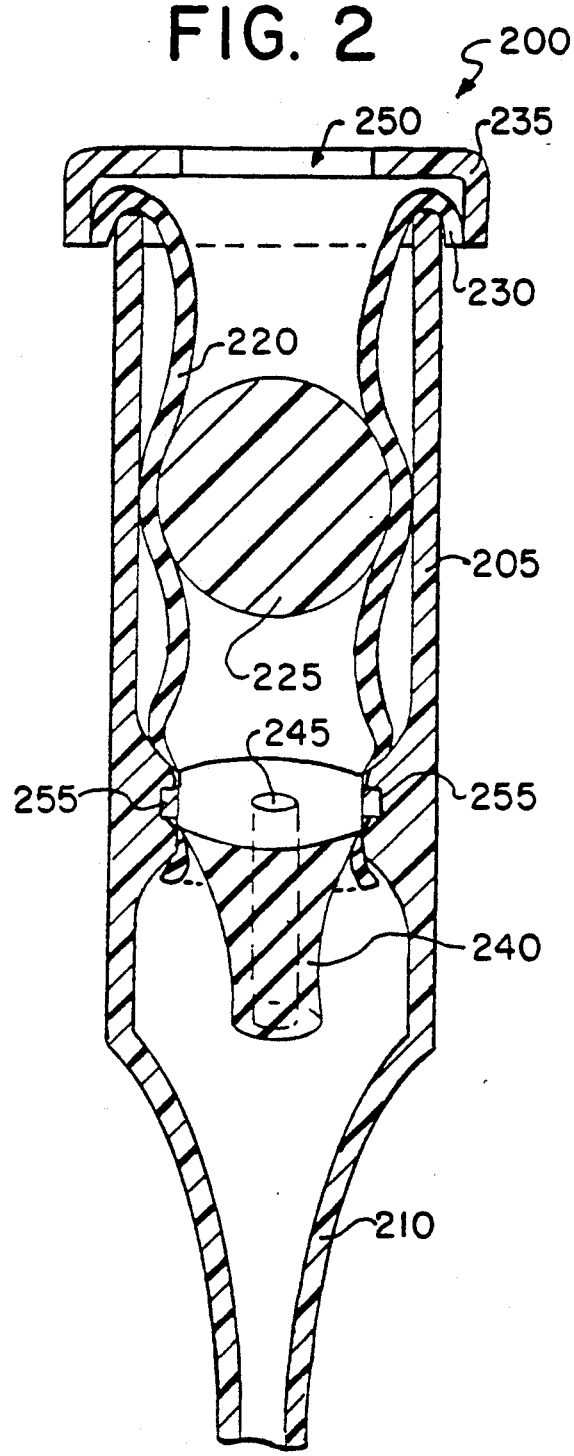
FIG. 2 is a cross-sectional view of a second valve arrangement illustrating a plug member for preventing fluid reflux.

FIG. 2 illustrates another fluid flow control means 200 in accordance with the invention. This embodiment also includes rigid plastic tubular housing 205, distal end 210, flexible silicone tube 220, disk member 225, and end cap 235 for securing the forward end 230 of silicone 220 to the forward end of housing 205. End cap 235 also includes aperture 250 which is smaller than disk member 225 and prevents the disk member from exiting the proximal end of housing 205.

In this embodiment, a different skirt member 240 is utilized. This skirt member 240 is in the form of a molded silicone plug having a central aperture 245 which allows a medical device to be inserted therein. This plug member 240 is retained in place in housing 205 by engaging the distal end of silicone tube 220 and shelf member 255. The inner diameter of shelf member 255 is smaller than disk member 225 so that the disk member cannot pass through the distal end of tube 220.

Assembly of the device of FIG. 2 is similar to that of FIG. 1. Again, housing 205 is made in two halves to facilitate access to interior portions for the purpose of assembly. Into one end of a silicone tube is placed the plug member 240, which is then placed on shelf member 255 in one of the housing halves. Next, disk member 225 may be inserted into the proximal end of tube 220 and placed midway between the forward end and shelf member of the housing. Next, the second housing half is placed over the first and the forward end 230 of tube 220 is rolled over the forward end of housing 205. Cap member 235 is then placed on the forward end of housing 205 to compress the end of tubing 230. If desired, the tubing ends of FIGS. 1 and 2 may be secured beneath the cap member by the use of a suitable adhesive. Finally, the housing halves of FIG. 2 are then sonically welded to form a one-piece assembly. Again, the fluid flow control device of FIG. 2 can be utilized as a separate or integral part of a catheter introducer or other device for directing fluid to or from a patient.

Another type plug member useful in the present invention is one which may be formed from the end of the silicone tube itself. To provide a plug member with an appropriate aperture, a stainless steel needle may be inserted in one end of a standard silicone (medical grade) tube after a disk member has been placed inside. The end of the tube can then be glued with a standard silicone adhesive until the ends are filled around the stainless steel needle. The needle can then be removed to create a small residual hole or outlet port which is equivalent in performance to the central aperture 245 of plug member 240. The disc member is retained in the tube since it cannot pass through the small aperture provided on the distal end. The tube can then be placed into the housing of either FIG. 1 or FIG. 2 or simply can be placed in a housing that does not include a shelf member while the proximal end of the flexible tube are retained in the forward end of the housing through the use of a cap member similar to that of 135 or 235. Other arrangements and modifications for forming this skirt or plug at the end of the silicone tube can be devised by one skilled in the art and all are considered to be within the scope of the present invention.

Figure 3:
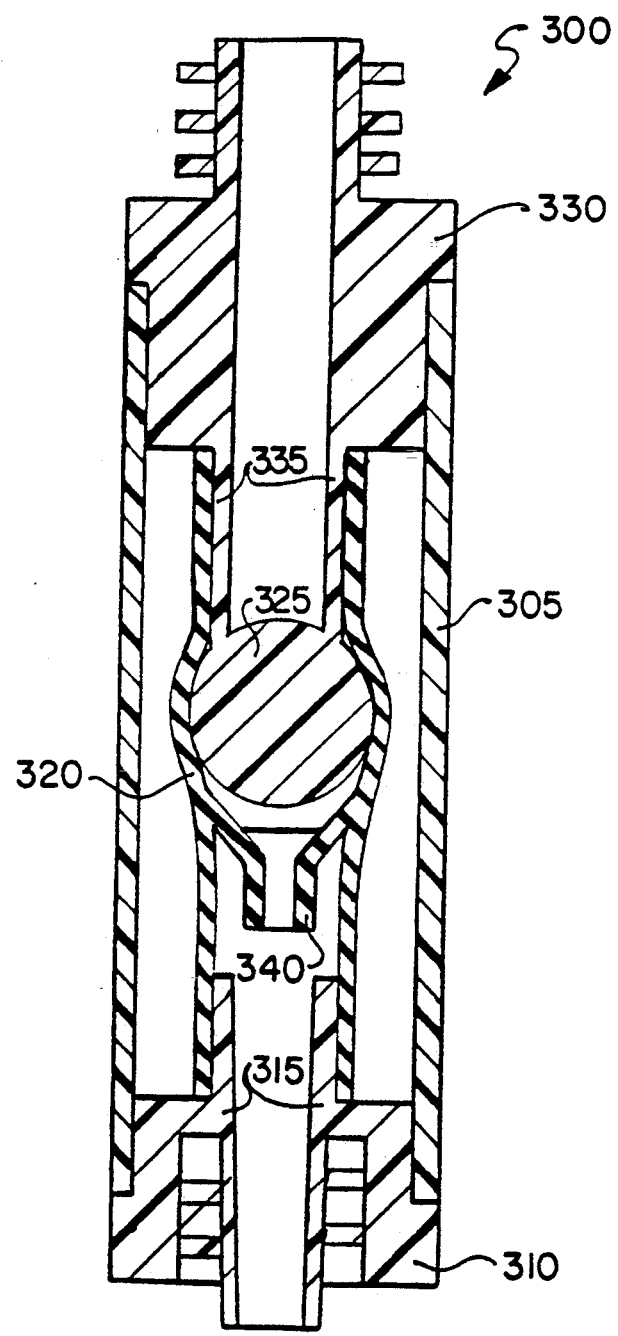
FIG. 3 is a cross-sectional view of a third valve arrangement illustrating another plug member for preventing fluid reflux.

FIG. 3 illustrates yet another embodiment of the present invention. In the fluid control means 300 of this embodiment, a clear relatively rigid plastic tube 305 is used as the outer housing of the device. One end of the housing is fitted with a male luer lock hub 310 for connection to a female luer lock hub on tubing or other fluid conduit means. An elastomeric tube 320 with an integral skirt member 340 is provided inside of the housing. The distal end of this tube is secured to nozzle 315 of locking hub 310 by an adhesive or other securing means.

At the opposite end of the housing a female luer lock hub 330 is provided. This hub 330 has an integral disk valve member 325 attached by arm members 335. Hub 330 also includes means for engaging a male luer lock hub of a fluid conduit or other fluid directing means. Disk valve 325 extends into tube 320 a sufficient distance and flattens the tube to prevent fluid flow or blood reflux therethrough. The proximal end of tube 320 is held in place by frictional forces caused by the attempted contraction of the tube around the arm members 335 of the female luer lock hub. The device of this embodiment is simply made by first forming the elastomeric tube 320 with an integral skirt either by molding, machining or suitable procedures. One end of the tube is then adhesively attached to the male luer lock nozzle prior to insertion of the luer lock hub into one end of housing 305. Thereafter, the female luer lock hub 330 is with integral disk member 325 is then inserted into the opposite end of the housing in a manner such that disk member 325 is inserted into tube 320.

It is to be understood that although the female luer lock hub 330 is shown with the disk means and male luer lock hub 330 is shown with a cylindrical nozzle 315, these features can be reversed if desired, that is the male luer lock hub 310 may be provided with extension arms for supporting the disk valve while the female luer lock hub can be provided with a nozzle for adhesively securing the opposite end of the silicone tube 320.

Accordingly, the present invention provides a number of elegant yet simplistic fluid flow control means which are usable in a wide variety of applications for directing fluids to or from a patient. And while numerous modifications and embodiments may be devised by those skilled in the art, it is intended that all such embodiments be covered by the appended claims.

What is claimed is:

1. A fluid control means comprising:
   tubular means having fluid input means and fluid output means connected by a bore constituting a flow channel, means for maintaining the bore in a normally closed position, the bore being forcible to an open position in response to insertion of a medical device into the fluid means and past the maintaining means, the maintaining means being constructed and arranged to return the bore to the closed position when the medical evidence device is removed therefrom, wherein the tubular means comprises a flexible tube and the maintaining means comprises a disc member positioned therein; and
   means for prevention of fluid reflux from the fluid output means toward the fluid input means when the bore is in the open position, wherein the fluid reflux prevention means comprises skirt means in communication with the fluid output means.

2. The fluid control means of claim 1 further comprising a housing surrounding the tubular means; means for attaching the fluid input means to a first end of the housing; and means for supporting the fluid output means within the housing.

3. The fluid control means of claim 2 wherein the supporting means of the housing is configured and positioned to have smaller dimensions than the disc member to prevent the disc member from exiting the fluid output means.

4. The fluid control means of claim 2 wherein the attaching means comprises a cap member which secures the input end of the flexible tube to the first end of the housing, wherein the cap member has an aperture of smaller dimension than the disc member to prevent the disc member from exiting the fluid input means of the flexible tube.

5. The fluid control means of claim 2 wherein the skirt means is integral with the fluid output means and comprises a diaphanous filamentous tubular structure which prevents fluid reflux towards the bore and is retained in position by the supporting means of the housing.

6. The fluid control means of claim 2 wherein the housing includes first and second longitudinal halves to facilitate assembly of the tubular means therein.

7. The fluid control means of claim 2 wherein the skirt means comprises a flexible, resilient plug member having a central aperture extending therethrough for forming a hemostatic seal about the medical device which is inserted therein.

8. The fluid control means of claim 7 wherein the plug member is cone shaped and is retained in communication with the fluid output means of the flexible tube by the supporting means of the housing.

9. The fluid control means of claim 2 wherein the disc member is mounted upon the fluid input attaching means and extends into the bore of the flexible tube.

10. The fluid control means of claim 9 wherein the fluid input attaching means further includes means for connecting the fluid control means to a first conduit.

11. The fluid control means of claim 2 wherein the fluid output means supporting means forms part of a housing exit port which includes means for connecting the fluid flow control means to a second conduit.

12. The fluid control means of claim 2 wherein the skirt means is positioned within the flexible tube and is attached thereto.

13. The fluid control means of claim 12 wherein the skirt member includes a cylindrical plug member having a generally central aperture therethrough and an external flange for attachment to the flexible tube.

14. A fluid flow control means comprising:
   tubular means comprising a flexible tube having fluid input means and fluid output means connected by a bore constituting a flow channel, means for maintaining the bore in a normally closed position comprising a disc member positioned in the flexible tube, the bore being forcible to an open position in response to insertion of a medical device into the fluid input means and past the maintaining means, the disc member being constructed and arranged to return the bore to the closed position when the medical device is removed therefrom;
   means for prevention of fluid reflux from the fluid output means toward the fluid input means when the bore is in the open position, said fluid reflux prevention means comprising skirt means in communication with the fluid output means; and
   a housing including first and second longitudinal halves for surrounding the tubular means; means for attaching the fluid input means to a first end of the housing; and means for supporting the fluid output means within the housing, said supporting means being configured and positioned to have smaller dimensions than the disc member to prevent the disc member from exiting the fluid output means of the flexible tube;

wherein the attaching means comprises a cap member which secures the input end of the flexible tube to the first end of the housing, with the cap member having an aperture of smaller dimensions than the disc member to prevent the disc member from exiting the fluid input means of the flexible tube;

wherein the skirt means is integral with the fluid output means and comprises a diaphanous filamentous tubular structure which prevents fluid reflux towards the bore and is retained in position by the supporting means of the housing.

15. A fluid flow control means comprising:

tubular means comprising a flexible tube having fluid input means and fluid output means connected by a bore constituting a flow channel, means for maintaining the bore in a normally closed position comprising a disc member positioned in the flexible tube, the bore being forcible to an open position in response to insertion of a medical device into the fluid input means and past the maintaining means, the disc member being constructed and arranged to return the bore to the closed position when the medical device is removed therefrom;

means for prevention of fluid reflux from the fluid output means toward the fluid input means when the bore is in the open position, said fluid reflux prevention means comprising skirt means in communication with the fluid output means; and a housing including first and second longitudinal halves for surrounding the tubular means; means for attaching the fluid input means to a first end of the housing; and means for supporting the fluid output means within the housing, said supporting means being configured and positioned to have smaller dimensions than the disc member to prevent the disc member from existing the fluid output means of the flexible tube;

wherein the attaching means comprises s cap member which secures the input end of the flexible tube to the first end of the housing, with the cap member having an aperture of smaller dimensions than the disc member from exiting the fluid input means of the flexible tube;

wherein the skirt means comprises a flexible, resilient plug member having a central aperture extending therethrough for forming a hemostatic seal about the medical device which is inserted therein, the plug member being cone shaped and retained in the communication with the fluid output means of the flexible tube by the supporting means of the housing.

16. A fluid flow control means comprising:

tubular means comprising a flexible tube having fluid input means and fluid output means connected by a bore constituting a flow channel, means for maintaining the bore in a normally closed position comprising a disc member positioned in the flexible tube, the bore being forcible to an open position in response to insertion of a medical device into the fluid input means and past the maintaining means, the disc member being constructed and arranged to return the bore to the closed position when the medical device is removed therefrom;

means for prevention of fluid reflux from the fluid output means toward the fluid input means when the bore is in the open position, said fluid input means when the bore is in the open position, said reflux prevention means comprising skirt means positioned within the flexible tube and including a cylindrical plug member having a generally central aperture therethrough and an external flange for attachment to the flexible tube;

a housing having first and second ends for surrounding the tubular means; first means for connecting the fluid input means to the first end of the housing, the first connecting means including first means for engaging a first conduit; and a second means for connecting the fluid output means to the second end of the housing, the second connecting means including second means for engaging a second conduit;

wherein the disc member is mounted upon the first connecting means and extends into the bore of the flexible tube.

17. The fluid flow control means of claim 16 wherein one of said first or second conduit engaging means includes a female locking member for engaging a male locking member of said conduit.

18. The fluid flow control means of claim 16 wherein one of said first or second conduit engaging means includes a male locking member for engaging a female locking member of said conduit.

* * * * *